United States Patent
Banks et al.

(10) Patent No.: US 7,561,989 B2
(45) Date of Patent: Jul. 14, 2009

(54) EXTRACTING PERFORMANCE METRICS FROM IMAGES

(75) Inventors: Gordon Banks, The Colony, TX (US); Ed Moon, Winter Springs, FL (US)

(73) Assignee: Procise, The Colony, TX (US)

( * ) Notice: Subject to any disclaimer, the term of this patent is extended or adjusted under 35 U.S.C. 154(b) by 0 days.

(21) Appl. No.: 11/732,498

(22) Filed: Apr. 3, 2007

(65) Prior Publication Data
US 2007/0282563 A1  Dec. 6, 2007

Related U.S. Application Data

(60) Provisional application No. 60/898,038, filed on Jan. 29, 2007, provisional application No. 60/789,089, filed on Apr. 4, 2006.

(51) Int. Cl.
*G06F 3/00* (2006.01)
(52) U.S. Cl. ............... 702/191; 702/179; 702/183; 702/190
(58) Field of Classification Search ............ 702/85, 702/94, 141, 143, 156, 159, 181, 179, 183, 702/190, 191; 250/208.1; 342/357.07; 375/240.16; 345/473, 474; 348/169–172
See application file for complete search history.

(56) References Cited

U.S. PATENT DOCUMENTS

| | | | | |
|---|---|---|---|---|
| 6,028,593 A * | 2/2000 | Rosenberg et al. | ........... | 345/156 |
| 6,295,367 B1 * | 9/2001 | Crabtree et al. | ............. | 382/103 |
| 6,532,264 B1 * | 3/2003 | Kahn | ................... | 375/240.16 |
| 6,744,403 B2 * | 6/2004 | Milnes et al. | .......... | 342/357.07 |
| 6,858,826 B2 * | 2/2005 | Mueller et al. | ........... | 250/208.1 |

OTHER PUBLICATIONS

Notification Concerning Transmittal of International Preliminary Report on Patentability in connection with PCT Patent Application No. PCT/US2007/008481.

* cited by examiner

*Primary Examiner*—Eliseo Ramos Feliciano
*Assistant Examiner*—Felix E Suarez

(57) ABSTRACT

Through the use of image processing and set-up calibration techniques, an accurate position of an object may be determined. Embodiments of the present disclosure measure a change in position over a known time interval. Accordingly, the change in position aids in measuring the object's metrics such as, for example, position, velocity, acceleration, maximum velocity, maximum acceleration and/or maximum deceleration. The object can be, for example, any person, individual body part, a group of body parts, a vehicle, or any other movable object.

20 Claims, 4 Drawing Sheets

EXTRACTING PERFORMANCE METRICS FROM IMAGES

CROSS-REFERENCE TO RELATED APPLICATIONS

This patent application claims priority under 35 U.S.C. §119(e) to U.S. Provisional Patent Application No. 60/898,038, entitled "EXTRACTING PERFORMANCE METRICS FROM IMAGES" filed Jan. 29, 2007, which is hereby incorporated by reference. This patent application claims priority under 35 U.S.C. § 119(e) to U.S. Provisional Patent Application No. 60/789,089, entitled "METHOD, APPARATUS AND COMPUTER PROGRAM PRODUCT FOR EXTRACTING OBJECT MOTION THROUGH IMAGE TRACKING" filed on Apr. 4, 2006, which is hereby incorporated by reference.

This patent application is related to U.S. Provisional Patent Application No. 60/532,833, entitled "SYSTEM AND METHOD FOR SPORTS ANALYSIS" filed on Dec. 24, 2003, which is hereby incorporated by reference.

TECHNICAL FIELD

This disclosure is generally directed to image processing and in particular to extracting performance metrics of objects from images.

BACKGROUND

Conventional methods of extracting object motion include image processing, motion detection, triangularization methods and camera projection mapping.

Currently, there are several methods for tracking moving targets. For example, velocity data can be obtained, for example, if you can measure the distance traveled by a moving object between two video frames. Accordingly, conventional methods fail to convert location information into motion based data for use in analysis and comparison. In particular, conventional systems fail to calculate, for example, the acceleration of a moving object at any given point in time.

Conventional systems often employ the use of an evaluation object affixed to the moving object to evaluate the velocity or acceleration of that moving object. Such systems require the evaluation object to include some sort of transmitter device or on-board telemetry. Accordingly, such systems lack the ability to perform processing of previously recorded performances.

There is therefore a need for improved systems for extracting object motion and metrics information.

SUMMARY

The present disclosure provides a system and method for extracting performance metrics of objects without the use of transmitters. The present disclosure may be used in any suitable application including, for example, sports evaluation, coaching, entertainment and medical applications.

Through the use of image processing and set-up calibration techniques, an accurate position of an object may be determined. Embodiments of the present disclosure measure a change in position over a known time interval. Accordingly, the change in position aids in measuring the object's metrics such as, for example, position, velocity, acceleration, maximum velocity, maximum acceleration and/or maximum deceleration. The object can be, for example, any person, individual body part, a group of body parts, a vehicle, or any other movable object on a video or digitally captured.

In one embodiment, the present disclosure provides a method of extracting performance metrics. The method includes inputting a digital video having at least one moving object and selecting a portion of the object. The method also includes determining the movement of the object through a pixel space and processing images of the object according to a user-defined set of calibration factors. The method could also include correlating pixel locations for the object and then outputting metric information about the portion of the object according to the correlated pixel locations.

In another embodiment, the present disclosure provides a system to extract performance metrics. The system includes a processor to input a digital video having at least one moving object. The processor also processes images of the object according to a user-defined set of calibration factors and outputs metric information related to the movement of the object through a pixel space.

In still another embodiment, the present disclosure provides a computer program embodied on a computer readable medium and operable to be executed by a processor. The computer program includes computer readable program code. The code includes inputting a digital video having at least one moving object and determining the movement of the object through a pixel space. The code also includes processing images of the object according to a user-defined set of calibration factors and correlating pixel locations for the object. The code further includes outputting metric information about the portion of the object according to the correlated pixel locations.

Other technical features may be readily apparent to one skilled in the art from the following figures, descriptions and claims.

BRIEF DESCRIPTION OF THE DRAWINGS

For a more complete understanding of this disclosure and its features, reference is now made to the following description, taken in conjunction with the accompanying drawings, in which.

DETAILED DESCRIPTION

The present disclosure provides a system and method for extracting performance metrics of objects without the use of transmitters. The present disclosure may be used in any suitable application including, for example, sports evaluation, coaching, entertainment and medical applications. Although the following description primarily describes embodiments of the present disclosure for use in conjunction with sports related applications, it should be understood that embodiments of the present disclosure may be used in a variety of other suitable applications.

The present disclosure evaluates objects contained in a live video stream and performs image processing algorithms on the user-selected object and tracks that object. Using information obtained by tracking the object, the present disclosure can calculate object metric data.

Figure 1:
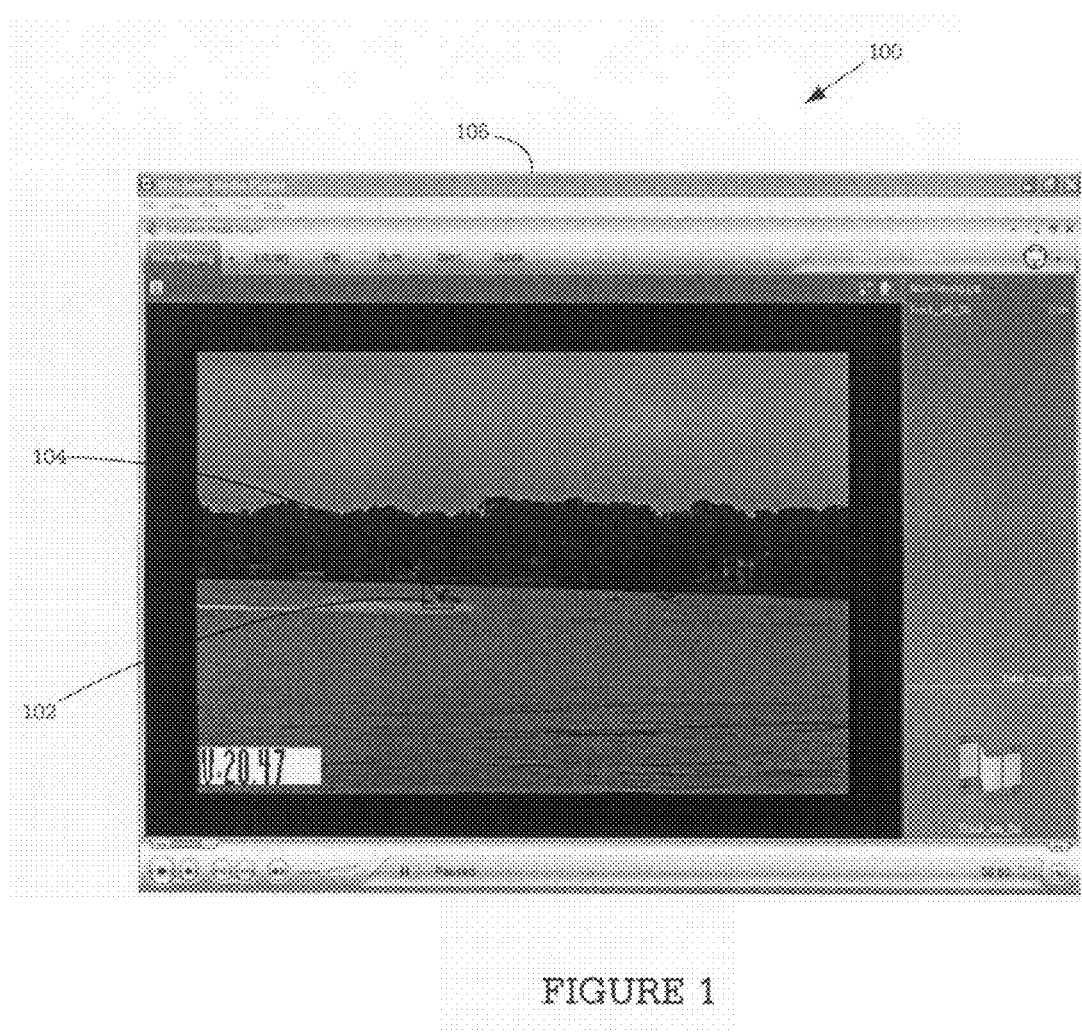
FIG. 1 is a snapshot of a sample video of a moving object shown on a suitable media player according to one embodiment, of the present disclosure.

FIG. 1 is a snapshot of a sample video 100 of a person 102 moving in a watercraft 104 shown on any suitable media player 106. It should be understood that video 100 may be any audio/visual file (AVI), video, film or movie that is stored in or is capable of being stored in digital form. Video 100 is shown for illustration purposes only. Video 100 could include any suitable moving objection according to one embodiment of the present disclosure.

One embodiment of the present disclosure traces an object's movement on video and can process the movements into a series of useful information. For example, the sample video 100 referred to in conjunction with the description accompanying FIG. 1 is first downloaded into a computer program according to one embodiment of the present disclosure. The moving object (for example, watercraft 104) is followed throughout the image plane through various motion detection algorithms and image correlations as described later in detail herein. The computer program referred to above is generally referred to herein as Trackometer™.

Figure 2:
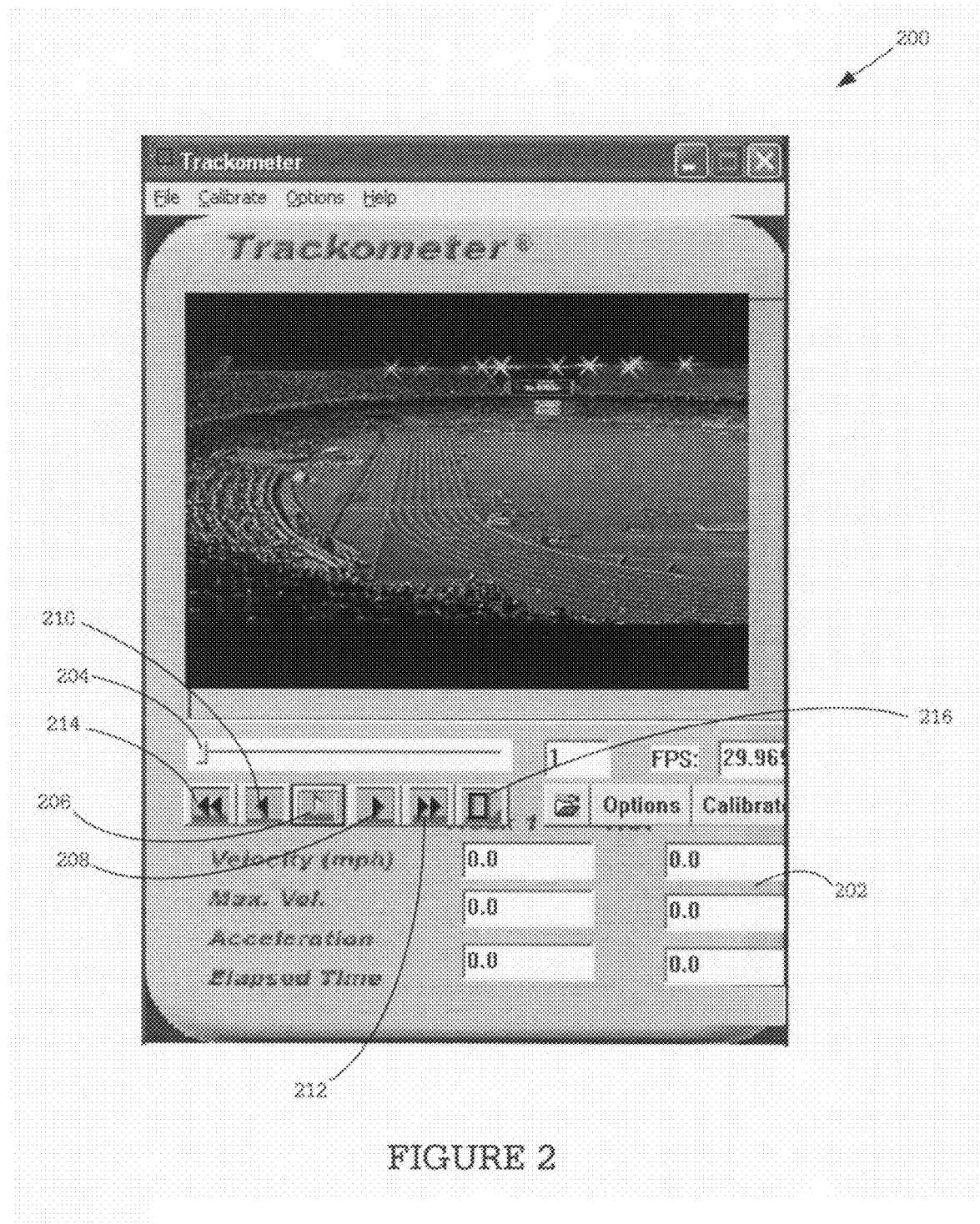
FIG. 2 is a sample graphical user interface for displaying the sample video of FIG. 1.

FIG. 2 is a sample snapshot of a graphical user interface (GUI) 200 for the main screen of the Trackometer™. In one embodiment, the Trackometer™ computer program evaluates the objects contained in the sample video based on the user-selected analysis. The GUI 200 is for illustration purposes only and may be in any suitable GUI or other interface.

Say for example, that the user desires to track an object and calculate data such as velocity and accelerations. The GUI 200 can display certain metrics important to the user in the metric display area 202. The user, using the Trackometer™ graphical user interface (GUI) 200, can also select the entire stream, select portions of or a specific series of frames from the sample video. Next, the user can select the specific object or group of objects within the video stream or frame to analyze.

Gui 200 also includes Trackometer™ playback controls are used to control the playback of the input file or sample video 100. The slider bar 204 illustrates the current relative frame position with respect to the beginning and ending of the input file or sample video 100. The running frame counter displays the current frame, and the total frames in the file. The playback controls include a "play" 206, "frame advance" 208, "frame reverse" 210, "forward" 212, "reverse" 214 and "stop" 216 capabilities.

In one embodiment, the "play" button 206 plays the input file 100 and preferably toggles from "play" to "pause" as the user views the file. The "stop" button 216 stops the input file 100 in the current frame. Preferably, after the "stop" button 216 is enabled, a subsequent election of the "play" button 206 will start the input file 100 from the beginning of the input file 100.

In one embodiment, the "frame advance" 208 or "frame reverse" 210 controls are used to advance or reverse frames, respectively, preferably in increments of 1 or 10. The increments are preferably selected by the user and allow viewing the entire or selected portions of the input file 100 on a frame by frame basis.

In one embodiment, a "frames per second" control gives the user the flexibility to choose the rate at which the input file will be recorded. By changing the "frames per second" control, the user can preferably change the value of the playback speed. The scale is proportional to the size of the input file 100. The current frame selected is indicated in a current frame window and can be changed by dragging the slider 204 to the portion of the input file 100 desired by the user. In addition, the playback speed may be increased or decreased by the user using the slider button 204.

It should be understood that other embodiments of the Trackometer™ playback controls may be used including, for example, embodiments in which the respective buttons have different functionality. In one embodiment, the user can define each of the control buttons differently from the standard set-up described earlier. For example, the Trackometer™ playback controls may include any other suitable controls such as, for example, a separate "pause" control or a "fast forward" control. As another example, the GUI 200 shown may be changed to suit a certain application or project. It should be understood that any suitable GUI 200 may be used as required according to embodiments of the present disclosure.

After selecting the object or group of objects to track, the video stream 100 may be played in real time and Trackometer™ can provide a real time analysis of the selected object's metrics. For example, suppose that the sample video stream 100 contained footage of a runner participating in a 100 yard dash. Suppose further that the runner's coaches had a desire to monitor and analyze the runner's injured left leg as the 100 yard dash was going on. A camera is set up to capture the runner's image as she attempts the 100 yard dash. The user can download the video directly to Trackometer™ and set it up to monitor the runner's left leg. As the 100 yard dash occurs, the coaches are able to track the performance of the runner's left leg in real time as the 100 yard dash is performed. In other words, the user (perhaps a coach or team manager) is able to monitor the velocity and acceleration of the runner's left leg in real time during the 100 yard dash.

The real-time information may be displayed in a superimposed results box, displayed as part of GUI 200 and/or recorded, downloaded and reviewed at a later time. The physical location of the result box on the image may be changed using the velocity overlay box portion 308a of the GUI 300a or 300b, for example, to a location most convenient to the user. The colors and background of the results box may be changed to suit the user's immediate needs using the GUI 300a or 300b. Other features may also be changed according to a user's preference.

Figures 3A, 3B:
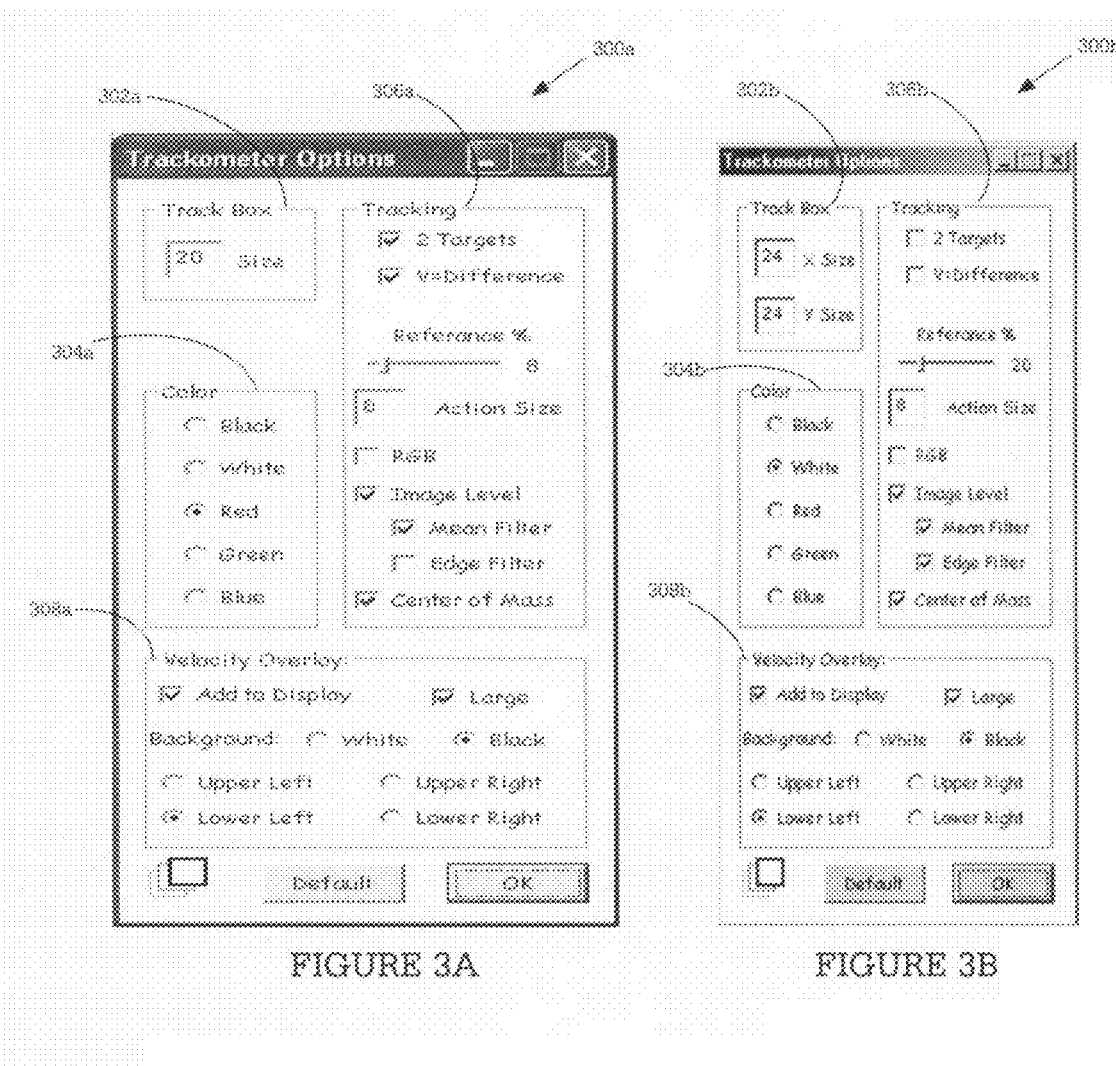
FIGS. 3A and 3B are sample graphical user interface for inputting the user desired system options according to one embodiment of the present disclosure.

The user interfaces shown in FIGS. 3A and 3B for Trackometer™ are alternative embodiments for GUI 300a and 300b, respectively, and are shown for illustration purposes only. Any suitable GUI 300a and 300b may be used according to the present disclosure.

GUI 300a and GUI 300b allow the user to choose several options while tracking a moving object. For example, a specialized area or "track box" area 302a or 302b may be designated to specify the image area to be tracked in order to isolate the object from other objects in the sample video 100 (e.g., tracking the left knee of a runner as opposed to the entire left leg). In other words, the track box 302a or 302b allows the user to input the size of the image to be analyzed. As another example, tracking may be specified to an object of a specific color (e.g., tracking a red shoe worn by a runner). In other words, the color box 304a or 304b may be used to input the specific color or colors required to be tracked.

There are several other tracking options available to the user. For example, the user can specify that Trackometer™ track the relative movement between two objects using tracking block 306a or 306b. For example, suppose the coaches in the above example wanted to track both of the runner's feet and the relative movement between the two. Trackometer™ can track such activity and provide information based on the relative movement of the runner's two feet. As another example, suppose the coaches in the above example wanted to track activity of the feet of their runner against the same of one of their competitors. Accordingly, Trackometer™ can track the relative motion of the two runners and provide a report of their performances with respect to each other. For example, the velocity differences between the two runner may be displayed by selecting the "V=Difference" option. The rate at which the Trackometer™ reference image is updated may also be set in the "Reference % " option.

Using tracking block 306a or 306b, a user can program Trackometer™ to identify and track the center of mass of an object. For example, suppose the coaches in the example given above wanted to track changes in the runner's center of mass as the race progressed or during discrete time periods, such as while running past bends in the race track. Trackometer™ can track such activity and provide a visual aid such as, for example, a providing a highlighted or colored area within the image to track the center of mass for the user of the program.

Using GUI 300a or 300b, and specifically tracking block 306a or 306b, a user can program Trackometer™ to adjust the image with different filters such as, for example, a mean filter or an edge filter. Thus, in one embodiment, the present disclosure can use different filters on the image to specify a particular part of an object. In addition, the "Action Size" option sets the size that the Trackometer™ tracks in the next frame.

In one embodiment, as the video is processed, the moving object and its location are determined. Once the position is determined, a velocity may be calculated through a change in position over time. After two or more velocities are calculated, an acceleration calculation is determined from the change in velocities. In one embodiment, the present disclosure provides Trackometer™ the ability to track any minimum and/or maximum values obtained over a period of time.

Calibration is necessary to ensure the accuracy and reliability of the Trackometer™. Calibration techniques essentially scale the program to the current image. In one embodiment of the present disclosure, for example, the user of the Trackometer™ first identifies a first sample object in the image of known size. The user enters the size of the sample object and inputs this into the Trackometer™ Calibration GUI. For example, the user enters the size of the sample object into the "Calibration 1" or CAL.1 field. After entering the size of the known object or objects, the user is then prompted to select two end points for a known distance. In order to calibrate the Trackometer™ accurately, care must be taken to select the ends of the object.

In one embodiment, if there is a second sample object of known size in the image, the user enters the size of the sample object into the "Calibration 2" or CAL2 field. Otherwise, the user has the option to calibrate the Trackometer™ over one known image using the "Same Cal. For Both Targets" box.

Calibration may be performed at any time when the Trackometer™ is in a paused or stopped state. For example, in one embodiment of the present disclosure, if an input file changes the "zoom" setting, analysis should be stopped and a calibration is warranted. Calibration may be performed on an image by image basis or by performing one calibration over a series of images in accordance with the present disclosure.

In one embodiment, the Trackometer™ takes into account the properties of the camera used for the input video. For example, Trackometer™ may take into account, the location, field of view, tilt, range, projection corners and pan of the camera. Each of or a desired subset of the factors may be used to calibrate the video image plan fed into the processing system. According, the as the camera moves, the calibration routine can adjust the subject object's position in, for example, real time. For example, the camera factors may affect the pixels-to-feet scale factor used by Trackometer™ in its calculations.

In another embodiment, if camera information is not available, a second calibration routine may be called upon. The second calibration routine places another image track on a known stationary object. Accordingly, a position delta can be generated off of the fixed object. Additionally, an object of known size can be used to provide additional input to produce the pixels-to-feet scale factor, if need be. It should be understood, however, that any number of suitable calibrations may be performed according to one embodiment of the present disclosure.

In addition, Trackometer™ can track the overall changes and calculations in a report form as a function of a desired factor. For example, the user can request a performance report which calculates the acceleration of an object at one second intervals. As another example, the user can request a performance report that plots acceleration calculations in graphical form. As still another example, the use can request a performance report that averages the acceleration at any given time over several repeat performances (e.g., a report of the runner's performances over five 100 yard dashes). In one embodiment, the present disclosure saves raw data and any performance reports into user-designated output files.

Trackometer™ has several other output formats. For example, in one embodiment, Trackometer™ may output a digital video file with object location and metric data overlaid in the file or video itself. Thus, a person observing the video can watch the video and access the metric data easily on the same screen. In another embodiment, the present disclosure may also output an independent data stream via, for example, a serial or Ethernet connection, with real-time data. Thus, in this embodiment, multiple users may have access to such metric data while observing the video. In still another embodiment, the present disclosure provides an output in which discrete data files contain just the performance statistics in a database or report format. It should be understood that any aggregated display or other suitable form of output may be used according to one embodiment of the present disclosure.

Figure 4:
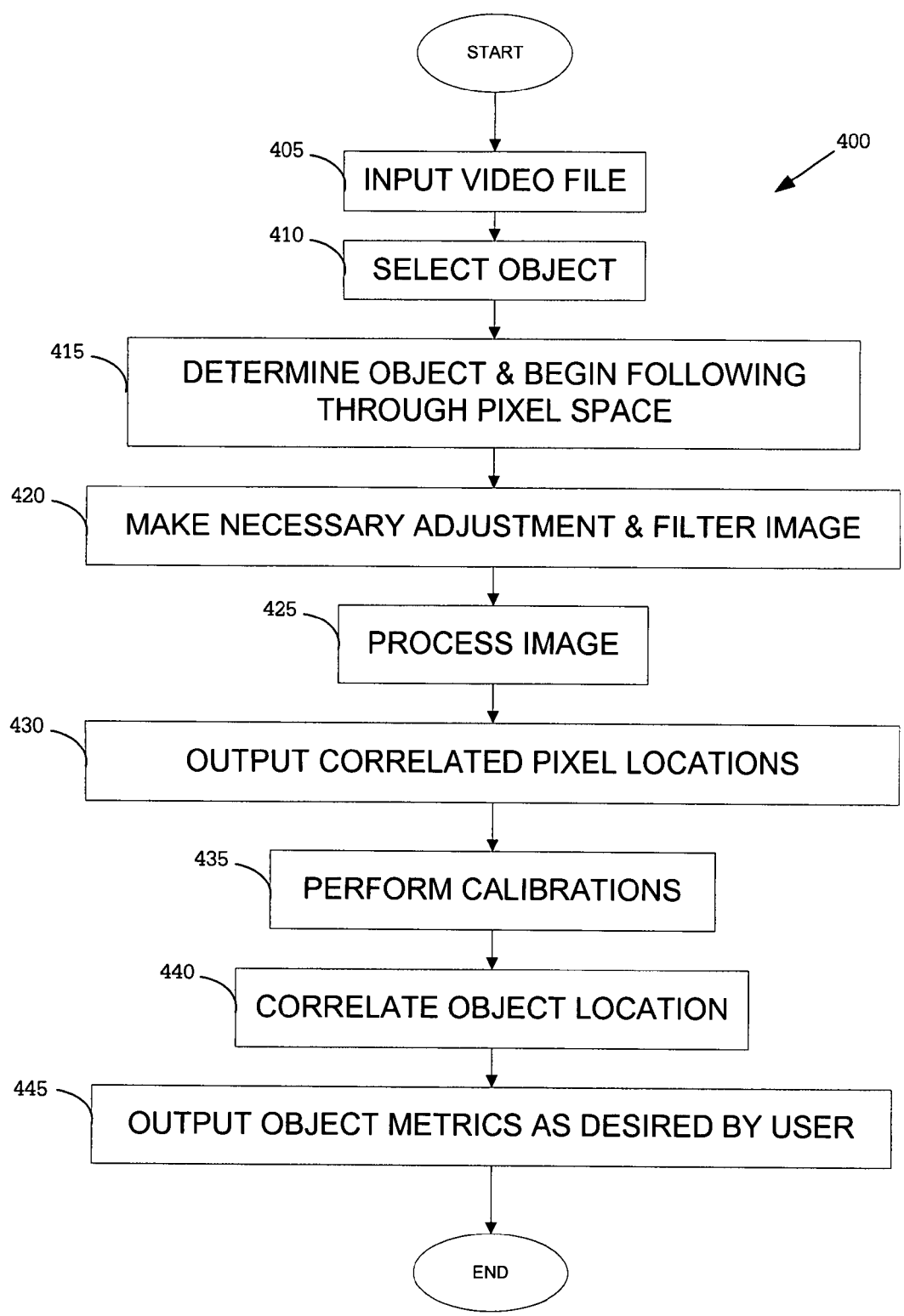
FIG. 4 is a somewhat simplified block diagram illustrating a method of extracting metric information from a moving object according to one embodiment of the present disclosure.

FIG. 4 is a somewhat simplified block diagram describing the image processing 400 according to one embodiment of the present disclosure. Image processing 400 is shown for illustration purposes only and other suitable image processing methods could be used according to one embodiment of the present disclosure.

After a video is input into the system in step 405, a user selects the object in the video to track in step 410. The system determines the object and follows the object through the pixel space in step 415. In step 420, the video may be adjusted for color, luminance. In addition, the video image may be filtered to render a specific form of the image. Any suitable adjustments and/or filtering could be used or applied according to the present disclosure.

In step 425, the video image may be processed to determine several factors such as, for example, the center of mass for the object. The detected motion is correlated for, for example, a minimum absolute difference and a specific X, Y location. In some embodiments, the object's location in 3D may also be possible. Finally, the system outputs the objects pixel locations in step 430. The system could output the pixel locations in any suitable form according to one embodiment of the present disclosure.

The pixel locations are input into a translator that takes into account the camera and projection factors described above and a calibration process is completed in step 435. Finally taking into account the pixel locations and pixels-to-feet factor, the object location is finally found.

In step 440, the output is then correlated to find a change in location (i.e., delta location or "Δ" location). From the change in location, the system is able to calculate metrics such as, for example, velocity, acceleration, a change in velocity (i.e., delta velocity or "Δ" velocity), and a change in acceleration (i.e., delta acceleration or "Δ" acceleration) at any given point in time. The information correlated can be output in any user-desired form such as, for example, graphs, charts, tables, reports or any combination thereof in step 445.

Embodiments of the present disclosure have many applications. For example, in certain embodiments the present disclosure may be used in the computer and arcade gaming market, entertainment related activities, children's applications, rehabilitation services and sporting activities.

In one embodiment, the present disclosure may be used to evaluate and predict an object's performance. For example, owners and managers can track the speed of a batter's swing or predict the dynamics of a golf swing. Owners and managers of sports teams can use embodiments of the present disclosure to provide an analysis of a current athlete or a perspective athlete. Owners and managers can also predict the performance of an athlete over time or analyze an athlete's performance before and after injuries. In addition, owners and managers can use embodiments of the present disclosure to assess and rank team members based on a performance ability index based on certain metrics obtained by the Trackometer™.

It may be advantageous to set forth definitions of certain words and phrases used in this patent document. The term "couple" and its derivatives refer to any direct or indirect communication between two or more elements, whether or not those elements are in physical contact with one another. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method of extracting performance metrics comprising:
    inputting data for a digital video of at least one moving object into a computer readable medium, the digital video including a plurality of frames corresponding to a pixel space through which pixel data for the object moves;
    selecting a portion of the object;
    processing pixel data corresponding to the selected portion of the object according to a user-defined set of calibration factors;
    correlating pixel locations for the selected portion of the object within the pixel space in at least two of the frames to determine movement of the selected portion of the object through the pixel space based upon changes in the pixel locations for the selected portion of the object relative to pixel data not corresponding to the selected object; and
    outputting metric information to the computer readable medium regarding movement of the selected portion of the object within the pixel space according to the correlated pixel locations.

2. The method according to claim 1, wherein the metric information comprises an acceleration of the object, the acceleration determined by examining movement of the selected portion of the object within the pixel space in the plurality of frames over a period of time, the time determined by a known frame rate of the digital video.

3. The method according to claim 2, wherein the acceleration of the object is determined for a specific point in time.

4. The method according to claim 1, wherein the metric information comprises a velocity of the object, the velocity determined by examining movement of the selected portion of the object within the pixel space in the plurality of frames over a period of time, the time determined by a known frame rate of the digital video.

5. The method according to claim 2, wherein the metric information comprises a maximum acceleration of the object.

6. The method according to claim 4, wherein the metric information comprises a maximum velocity of the object.

7. The method according to claim 1 further comprising:
    scaling the image of the object to a second object, the second object having a known size.

8. The method according to claim 1 further comprising:
    storing the metric information in a memory; and
    comparing a second set of metric information to the stored metric information.

9. The method according to claim 8 further comprising:
    outputting a report describing a relationship between the metric information and the second set of metric information.

10. A system to extract performance metrics comprising:
    a digital video recorded on a computer readable medium, the digital video including a plurality of frames corresponding to a pixel space through which pixel data for the object moves; and
    a processor operable to:
        input the digital video of at least one moving object;
        select a portion of the object;
        process pixel data corresponding to the selected portion of the object according to a user-defined set of calibration factors;
        correlate pixel locations for the selected portion of the object within the pixel space in at least two of the frames to determine movement of the selected portion of the object through the pixel space based upon changes in the pixel locations for the selected portion of the object relative to pixel data not corresponding to the selected object; and
        output metric information regarding movement of the selected portion of the object within the pixel space according to the correlated pixel locations.

11. The system according to claim 10, wherein the metric information comprises an acceleration of the object, the acceleration determined by examining movement of the selected portion of the object within the pixel space in the plurality of frames over a period of time, the time determined by a known frame rate of the digital video.

12. The system according to claim 11, wherein the acceleration of the object is determined for a specific point in time.

13. The system according to claim 10, wherein the metric information comprises a velocity of the object, the velocity determined by examining movement of the selected portion of the object within the pixel space in the plurality of frames over a period of time, the time determined by a known frame rate of the digital video.

14. The system according to claim 11, wherein the metric information comprises a maximum acceleration of the object.

15. The system according to claim 13, wherein the metric information comprises a maximum velocity of the object.

16. The system according to claim 10 the processor scales the image of the object to a second object, the second object having a known size.

17. The system according to claim 10 further comprising:
a memory to store the metric information in a memory.

18. The system according to claim 17, wherein the processor compares a second set of metric information to the stored metric information.

19. The system according to claim 18, wherein the processor outputs a report describing a relationship between the metric information and the second set of metric information.

20. A computer program embodied on a computer readable medium and operable to be executed by a processor, the computer program comprising computer readable program code, the code comprising:
inputting a digital video of at least one moving object, the digital video including a plurality of frames corresponding to a pixel space through which pixel data for the object moves;
selecting a portion of the object;
processing pixel data corresponding to the selected portion of the object according to a user-defined set of calibration factors;
correlating pixel locations for the selected portion of the object within the pixel space in at least two of the frames to determine movement of the selected portion of the object through the pixel space based upon changes in the pixel locations for the selected portion of the object relative to pixel data not corresponding to the selected object; and
outputting metric information regarding movement of the selected portion of the object within the pixel space according to the correlated pixel locations.

* * * * *